United States Patent
Blaine

(10) Patent No.: US 6,336,741 B1
(45) Date of Patent: Jan. 8, 2002

(54) METHOD AND APPARATUS OF MODULATED-TEMPERATURE THERMOGRAVIMETRY

(75) Inventor: Roger L. Blaine, New Castle, DE (US)

(73) Assignee: TA Instruments, Inc., New Castle, DE (US)

( * ) Notice: Subject to any disclaimer, the term of this patent is extended or adjusted under 35 U.S.C. 154(b) by 0 days.

(21) Appl. No.: 09/597,687

(22) Filed: Jun. 19, 2000

Related U.S. Application Data

(63) Continuation of application No. 09/105,238, filed on Jun. 26, 1998, now Pat. No. 6,113,261.
(60) Provisional application No. 60/051,169, filed on Jun. 27, 1997.

(51) Int. Cl.$^7$ .......................... G01N 25/00; G01G 23/04
(52) U.S. Cl. ............................. 374/14; 374/15; 374/45; 177/245
(58) Field of Search ................................ 374/14, 11, 33, 374/43, 31, 16, 10, 12–13, 55, 56, 45, 15; 73/15 B; 177/150, 245, 25.13, 25.14, 25.9

(56) References Cited

U.S. PATENT DOCUMENTS

| | | | |
|---|---|---|---|
| 3,902,354 A | * 9/1975 | Harlan et al. ................ 73/158 |
| 4,606,649 A | 8/1986 | Mikhail ........................ 374/10 |
| 4,693,252 A | 9/1987 | Thoma et al. ............... 128/400 |
| 4,783,174 A | * 11/1988 | Gmelin et al. .............. 374/33 |
| 4,817,745 A | 4/1989 | Beshoory ..................... 374/14 |
| 4,833,688 A | * 5/1989 | Smith .......................... 374/42 |
| 4,848,093 A | 7/1989 | Simmonds et al. .......... 62/49.1 |
| 4,871,961 A | 10/1989 | Kersten et al. ............. 323/267 |
| 5,165,792 A | 11/1992 | Crowe et al. ................ 374/10 |
| 5,215,377 A | 6/1993 | Sugano ........................ 374/14 |
| 5,224,775 A | 7/1993 | Reading et al. .............. 374/11 |
| 5,306,087 A | 4/1994 | Nakamura et al. ........... 374/14 |
| 5,321,719 A | * 6/1994 | Reed et al. ................... 374/14 |
| 5,368,391 A | 11/1994 | Crowe et al. ................ 374/10 |
| 5,466,066 A | 11/1995 | Hidaka ........................ 374/14 |
| 5,826,983 A | 10/1998 | Nakamura et al. ........... 374/14 |
| 6,007,240 A | * 12/1999 | Price ........................... 374/55 |
| 6,146,012 A | * 11/2000 | Nakamura et al. ........... 374/10 |
| 6,170,984 B1 | * 1/2001 | Schawe et al. .............. 374/10 |

FOREIGN PATENT DOCUMENTS

| DE | 33 04 322 A1 | 8/1984 |
| DE | 43 36 973 A1 | 5/1995 |
| DE | 195 04 470 A1 | 8/1996 |

* cited by examiner

Primary Examiner—Diego Gutierrez
Assistant Examiner—Gail Verbitsky
(74) Attorney, Agent, or Firm—Shaw Pittman LLP

(57) ABSTRACT

A method for controlling a thermogravimetry experiment and for quantitatively determining kinetic constants for decomposition or volatilization reactions using periodic forcing (modulated) temperature functions. A temperature program having a linear part and a periodically varying part superimposed thereon is applied to a sample in a thermogravimetric analyzer. The resulting mass signal is deonvoluted, or separated, into one or more deconvoluted signals.

10 Claims, 3 Drawing Sheets

METHOD AND APPARATUS OF MODULATED-TEMPERATURE THERMOGRAVIMETRY

The present application is a continuation of U.S. application Ser. No. 09/105,238, filed June 26, 1998, now U.S. Pat. No. 6,113,261, which is hereby incorporated by reference herein in its entirety.

The present application hereby claims benefit of the priorty date of U.S. Provisional Application No. 60/051,169, which was filed on Jun. 27, 1997.

FIELD OF THE INVENTION

The present invention relates to methods for controlling the temperature program used with thermogravimetric analyses.

BACKGROUND OF THE INVENTION

Kinetics is the study of the dependence of a chemical reaction on time and temperature. Kinetic reactions are often described using two equations. The first of these is known as the rate equation and describes the relationship between the rate of reaction, time and amount of material. For homogeneous decomposition or volatilization reactions, the reaction is almost universally found to follow the general rate equation which takes the form:

$$\frac{d\alpha}{dt} = k(T)[f(\alpha)]^n \tag{1}$$

Where:
$\alpha$=reaction fraction
$d\alpha/dt$=rate of reaction
$k(T)$=rate constant at a given temperature T
T=absolute temperature
$f(\alpha)$=kinetic expression
n=reaction order The second equation describing kinetic reactions details the dependence of the rate constant on temperature and is known as the Arrhenius equation.

$$k(T)=Ze^{(-E/RT)} \tag{2}$$

Where:
z=the pre-exponential factor
e=natural logarithm base
E=activation energy
R=gas constant The rate and Arrhenius equations may be combined into a single form:

$$\frac{d\alpha}{dt} = Z[f(\alpha)]^n e^{(-E/RT)} \tag{3}$$

The parameters E, Z and n are called kinetic constants and may be used to model the dependence of a chemical reaction on time and temperature.

Thermogravimetry is used to obtain kinetic constants of decomposition or volatilization reactions using one of several common methods. One approach is known as the "factor jump" method where the temperature of the test specimen is "stepped" between two or more isothermally held temperatures in the weight loss region. The rate of weight loss ($d\alpha/dt$) at each of the isothermal regions may be substituted into equation (3), along with the respective isothermal temperature(T). Any two equations for adjacent steps may then be examined as their ratio and the resultant form may be solved for activation energy.

$$E = \frac{RT_1T_2}{T_1-T_2}\left[\ln\frac{d\alpha_1}{d\alpha_2} + \ln\frac{f(\alpha_2)}{f(\alpha_1)}\right] \tag{4}$$

Where:
$d\alpha_1$=rate of weight loss at temperature $T_1$
$d\alpha_2$=rate of weight loss at temperature $T_2$
$f(\alpha_1)$=kinetic expression at the value of $d\alpha_1$
$f(\alpha_2)$=kinetic expression at the value of $d\alpha_2$ Should the values for $d\alpha_1$ and $d\alpha_2$ be extrapolated to a common conversion level, then $\alpha_1=\alpha_2$ and $\ln[f(\alpha_1)/f(\alpha_2)]=0$, reducing equation (4) to a more easily evaluated form:

$$E = \frac{RT_1T_2\ln(d\alpha_1/d\alpha_s)}{T_1-T_2} \tag{5}$$

SUMMARY OF THE INVENTION

In thermal analysis, the temperature rate of change is a forcing function (or independent parameter) which produces some physical or chemical change in a test specimen resulting in a measured response (or dependent experimental) parameter such as weight change. A linear temperature ramp is the most commonly used of these forcing functions. U.S. Pat. No. 5,224,775, which is incorporated by reference herein, however, introduced to thermal analysis (including thermogravimetry), the concept of a modulated-temperature forcing function. In the modulated temperature approach, a linear temperature ramp is modulated with a sinusoidal heating rate oscillation. This periodic temperature function produces corresponding oscillatory output response signal proportional to some physical property of the material under test. Deconvolution of the resultant experimental parameter signals leads to analytical information unavailable from the linear ramp forcing function alone.

In this invention, a sinusoidal heating rate oscillation is applied to thermogravimetry to obtain dependent parameters signals useful for the obtaining of kinetic information. Specifically, if the temperature is changed in an sinusoidal fashion around an average temperature (T), then the values of the peak temperatures may be given (T+A) and (T−A), where A is the half peak-to-peak amplitude. This forcing function produces a corresponding oscillatory rate of weight change and logarithm of the rate of weight change response signals. These terms may be substituted into equation (4) to obtain:

$$E = \frac{R(T^2-A^2)}{2A}\left[\ln\frac{d\alpha_1}{d\alpha_2} + \ln\frac{f(\alpha_2)}{f(\alpha_1)}\right] \tag{6}$$

A mathematical deconvolution technique, such as a discrete fast Fourier transformation, may be applied to the forcing and response functions to obtain average and amplitude values on a continuous bases. If average temperature oscillation (T), temperature amplitude (2A), rate of weight loss ($d\alpha/dt$) and amplitude of the logarithm of rate of weight loss [L=ln ($d\alpha_1/d\alpha_2$)] are obtained for constant conversation values [i.e., $\alpha_1=\alpha_2$ and $\ln[f(\alpha_1)/f(\alpha_2)]=0$], equation (6) reduces to:

$$E = \frac{R(T^2 - A^2)L}{2A} \qquad (7)$$

This equation is independent of the form of the reaction equation and may be said to be model independent. If, however, a model is selected then other kinetic parameters, such as the pre-exponential factor and reaction order, may be obtained. Homogeneous decomposition or volatilization reactions are almost universally found to follow first order kinetics where n=1 and the logarithm of the pre-exponential factor equals $\ln [d\alpha/(1-\alpha)]+E/RT$.

The use of continuously deconvoluted, or separated, values of the oscillatory forcing functions and corresponding oscillatory response provides, then, for the continuous generation of activation energy and pre-exponential factor throughout the reaction range.

Further, U.S. Pat. No. 5,165,792, which is incorporated by reference herein, describes how the heating rate (temperature forcing function) in thermal analysis may be adjusted according to the rate of change of a dependent parameter. In thermogravimetry, the temperature of the experiment is adjusted to maintain an average rate of weight change. A second part of this invention involves the control of the average experimental temperature using the average rate of weight change generated by the deconvolution.

According to equation (1), the rate of the reaction will decrease as the amount of reactant is consumed. To compensate for this rate of weight change reduction, the average temperature is adjusted during the reaction according to the average rate of weight change obtained from the deconvoluted response signal. This provides a smooth, continuous, and rapid change in the average temperature during regions where no weight change is observed but then a decrease in the average temperature change rate where weight changes reaction occur. Once a weight change is complete, the average temperature of the modulated temperature experiment is automatically increased until another weight change region is observed or the maximum temperature of the experiment is reached.

DETAILED DESCRIPTION OF THE INVENTION

Figure 1:
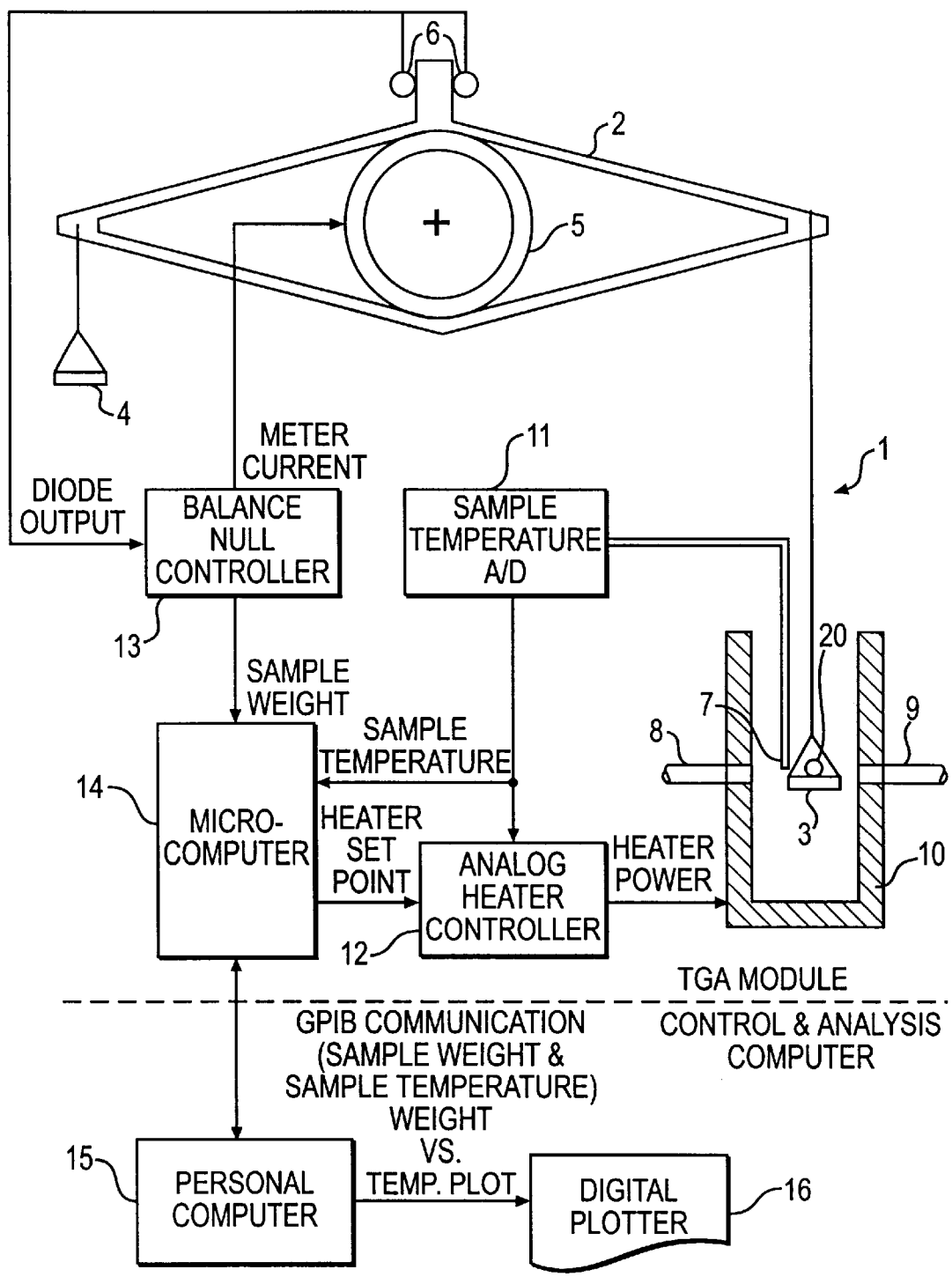
FIG. 1 illustrates schematically a thermogravimetric analyzer for use in the present invention.

FIG. 1 is a schematic illustration of a thermogravimetric analyzer (TGA) for that can be used with the present invention. TGAs are well known in the art, and will be described only in a overview sense herein. An example TGA for use in the present invention is the TGA 2950 from TA Instruments, Inc. of New Castle, Del. A more detailed description can be found in U.S. Pat. No. 5,165,792, which is hereby incorporated in its entirety, and in U.S. Pat. No. 5,368,391, which is hereby incorporated by reference in its entirety. A sample 20 is placed at a sample position 3 in the TGA. Elements 1–6 comprise an electrobalance in which a sample at position 3 is balanced by a counterbalance 4 and a torque motor 5. As sample 20 loses weight, the force on torque motor 5 is changed so that the system remains in balance. The signal to torque motor 5 is proportional to the mass remaining of the sample.

The sample is surrounded by a furnace, or oven, composed of elements 7–10. The temperature of the furnace is controlled by a heater controller 12. Control is preferably performed using a feed back control system comprising a temperature sensor 7 and a heater set point generated by a microcomputer 14. That is, microcomputer 14 calls for the furnace to be at a particular temperature. The actual furnace temperature is determine by temperature sensor 7. Heater controller 12 provides power to the furnace so that the difference between the set point and the actual temperature approaches zero.

The temperature of the sample determined by temperature sensor 7, and the weight information provided by the electrobalance, determined by a balance null controller 13, are the primary signals generated by the TGA. These signals are preferably treated further by a computer 15 to obtain other information such as rates of change of mass. These additional signals can be fed back to the microcomputer to help generate the desired temperature program. A more detailed description of FIG. 1 is given in U.S. Pat. No. 5,165,792 at column 7, lines 9–46, and in U.S. Pat. No. 5,368,391 at column 7, lines 10–50.

In the present invention the temperature program can be characterized as having a modulation period, a modulation amplitude and an underlying heating or cooling rate. Preferably, the temperature program has a linearly varying part onto which a periodically varying part is superimposed to created a "modulated" temperature program. The modulated temperature program has a modulation amplitude, modulation period or frequency and underlying heating or cooling rate. Appropriate signals for the periodically varying part include, but are not limited to, a triangle wave, a square wave, a sinusoidal wave and a saw tooth wave or any combination thereof.

The temperature program can be selected in a variety of ways. Preferably, the modulation amplitude, modulation period or frequency and underlying heating or cooling rate are selected explicitly by the user. Similarly, a user can select parameters which microcomputer 14 of computer 15 then converts into a modulation amplitude, modulation frequency or period and underlying heating or cooling rate.

Preferably the linearly varying part and the periodically varying part are summed to form the temperature program of the present invention. The summation can be performed in a well-known manner using analog and/or digital components.

Figure 2:
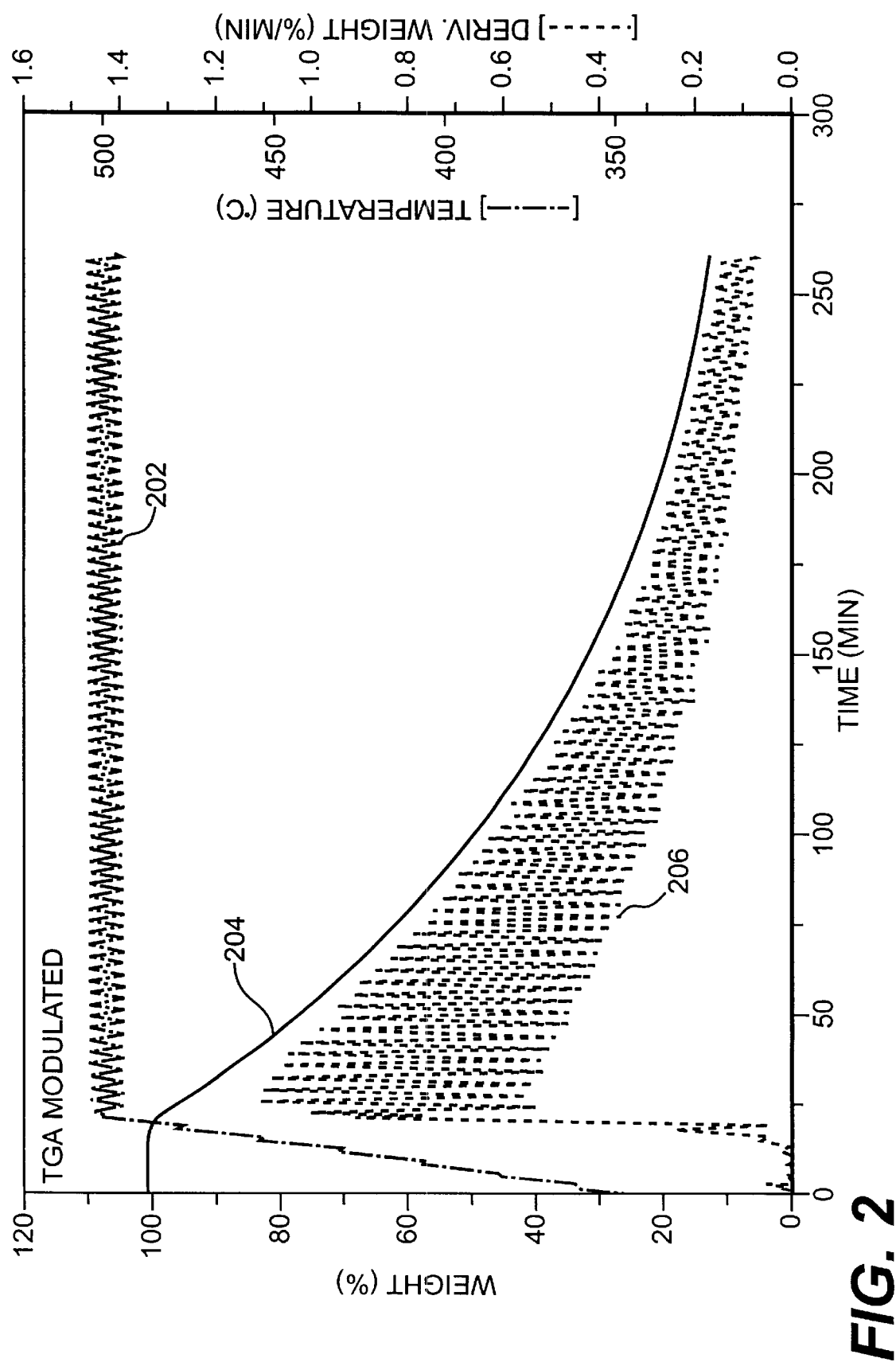
FIG. 2 is a plot showing the decomposition of poly (tetrafluoroethylene) using quasi-isothermal temperature modulation.
Figure 3:
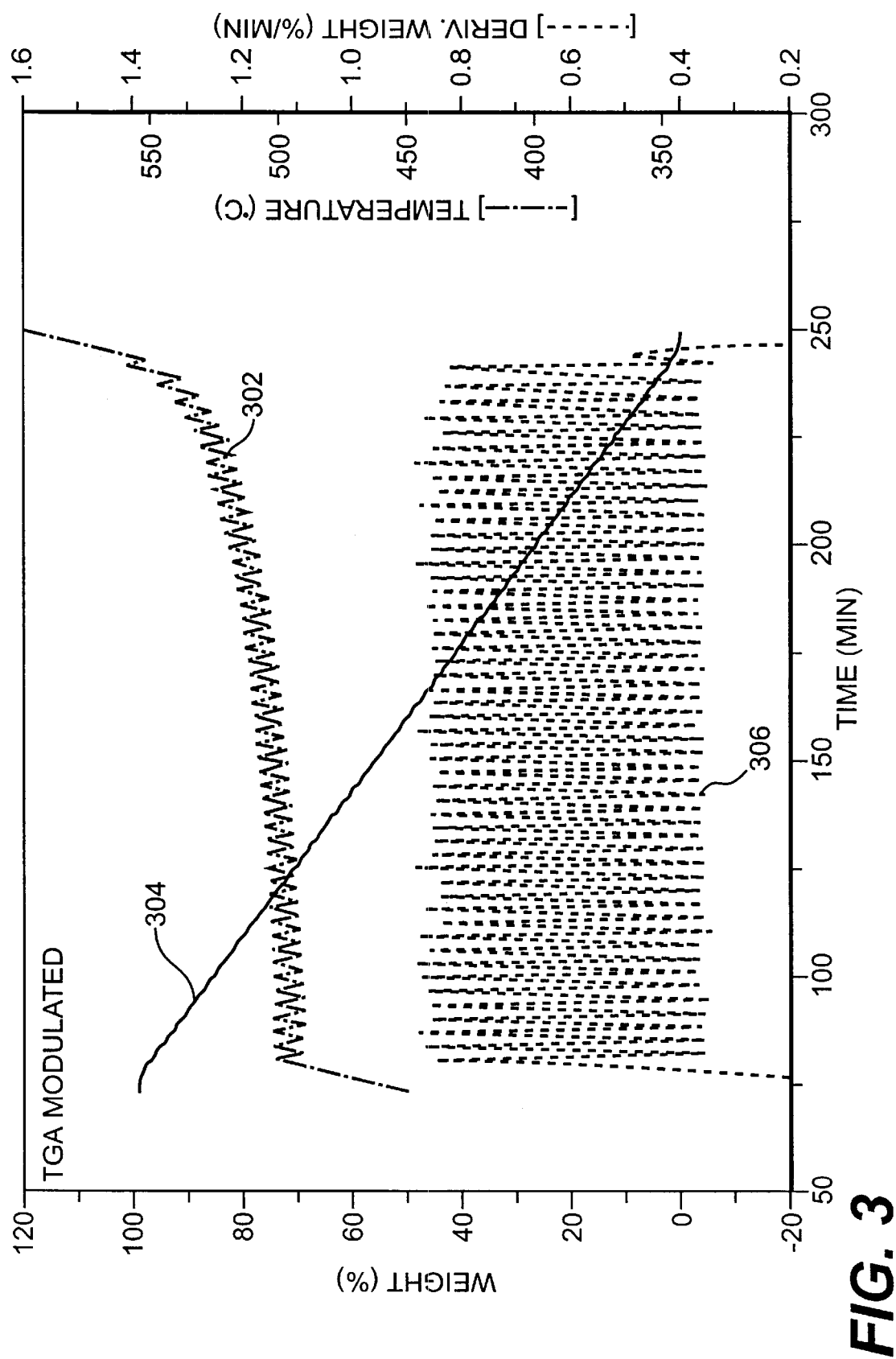
FIG. 3 is a plot showing the decomposition of poly (tetrafluoroethylene) using temperature modulation and constant average rate of weight loss.

The present invention is illustrated herein through the use of two examples. The results of the examples are shown in FIGS. 2 and 3. FIGS. 2 and 3 display three signals on the Y-axis as a function of time (the X-axis). In each Figure, the percent of the original weight of the sample is presented in the middle line, the temperature of the sample is shown in the upper line, and the rate of change of the percent original sample weight is presented in the lower line.

In the example shown in FIG. 2, the temperature was sinusoidally modulated with and amplitude of ±5° C. and a period of 200 seconds. This modulated temperature was superimposed over an underlying temperature ramp at 7° C./min, starting from an ambient temperature up to 500° C. and held there for approximately 200 minutes. The temperature program is shown as curve 202. At this quasi-isothermal region, the weight of the sample decreases in an exponential fashion from the 100% original weight to about 20%. This weight is shown as a percentage of the original weight in curve 204. The rate of weight loss is not smooth but has short term variation in response to the sinusoidal temperature oscillations as shown in the rate of weight change curve. The rate of weight loss in percent of original weight per minute is shown in curve 206. The average rate of weight loss and the amplitude of the oscillatory rate of weight loss are observed to decrease with increasing conversion (decreasing weight percent).

In the example shown in FIG. 3, the temperature was increased at 7° C./min until the rate of sample weight loss reaches 0.8%/min. Once the limit was reached, the temperature was cooled at 7° C./min until the rate of weight loss fell below 0.4%/min. This heat/cool cycle was repeated, producing a sawtooth temperature modulation of amplitude ±5° C. and a period of 200 seconds around an average temperature. The temperature program is illustrated as curve 302. Once the sample was consumed, the temperature was once again increased at a rate of 7° C. until another weight loss is observed or the temperature limit is reached. This approach produces a temperature program where the average temperature is controlled to maintain a constant average rate of weight loss. The weight of the sample as a percentage of original weight is shown in curve 304. The rate of weight loss as a percentage of the original weight per minute is shown in curve 306.

What is claimed is:

1. A system for determining a kinetic parameter of a sample, comprising:

an oven having a heater for heating the sample according to a temperature program that can be characterized by a modulation amplitude and a modulation frequency or modulation period;

means for determining an average temperature and temperature amplitude of the temperature program;

means for determining a rate of weight loss and amplitude of the logarithm of the rate of weight loss of a weight change signal of the sample in response to heating; and means for determining at least one kinetic parameter using the average temperature, temperature amplitude, rate of weight loss and amplitude of the logarithm of the rate of weight loss.

2. The system recited in claim 1, wherein the temperature program is also characterized by an underlying heating rate.

3. The system recited in claim 1, wherein a first portion of the temperature program is characterized by an underlying heating rate and a second portion of the temperature program is characterized by quasi-isothermal operation.

4. The system recited in claim 1, further comprising means for modifying the heating of the sample in accordance with the rate of weight loss.

5. The system recited in claim 1, wherein the at least one kinetic parameter is one or more of activation energy, reaction order and pre-exponential factor.

6. A method for determining a kinetic parameter of a sample, comprising the steps of:

heating the sample according to a temperature program that can be characterized by a modulation amplitude and a modulation frequency or modulation period;

determining an average temperature and temperature amplitude of the temperature program;

determining a rate of weight loss and amplitude of the logarithm of the rate of weight loss of a weight change signal of the sample in response to heating; and determining at least one kinetic parameter using the average temperature, temperature amplitude, rate of weight loss and amplitude of the logarithm of the rate of weight loss.

7. The method recited in claim 6, wherein the temperature program is also characterized by an underlying heating rate.

8. The method recited in claim 6, wherein a first portion of the temperature program is characterized by an underlying heating rate and a second portion of the temperature program is characterized by quasi-isothermal operation.

9. The method recited in claim 6, further comprising the step of modifying the heating of the sample in accordance with the rate of weight loss.

10. The method recited in claim 6, wherein the at least one kinetic parameter is one or more of activation energy, reaction order and pre-exponential factor.

* * * * *